United States Patent [19]
Kobler

[11] 3,946,737
[45] Mar. 30, 1976

[54] CATAMENIAL TAMPON
[75] Inventor: Paul Kobler, Lynbrook, N.Y.
[73] Assignee: Paul Kobler, Lynbrook, N.Y.
[22] Filed: July 5, 1974
[21] Appl. No.: 466,180

[30] Foreign Application Priority Data
May 25, 1973  Switzerland.......................... 7492/73

[52] U.S. Cl. .............................................. 128/285
[51] Int. Cl.² ........................................ A61F 13/20
[58] Field of Search ........... 128/285, 270, 260, 263, 128/269

[56] References Cited
UNITED STATES PATENTS

| | | | |
|---|---|---|---|
| 2,499,414 | 3/1950 | Rabell................................. | 128/285 |
| 2,877,767 | 3/1959 | Kramer............................... | 128/270 |
| 2,965,101 | 12/1960 | Schirmer et al. .................... | 128/285 |
| 3,135,262 | 6/1964 | Kobler............................ | 128/263 X |
| 3,674,029 | 7/1972 | Bates .................................. | 128/285 |

FOREIGN PATENTS OR APPLICATIONS

| | | | |
|---|---|---|---|
| 527,827 | 10/1940 | United Kingdom................. | 128/285 |
| 500,742 | 2/1939 | United Kingdom................. | 128/270 |
| 224,782 | 3/1943 | Switzerland......................... | 128/285 |

*Primary Examiner*—Aldrich F. Medbery

[57]  ABSTRACT

A catamenial tampon of compressed absorbent material manufactured in such a way, that a bulge is created in the center area of said tampon, said bulge having part of the fibers loosened creating therewith a softer surface on the bulge compared with the harder sections of the two neighboring cylindrical areas, whereby irritation of the vagina walls is avoided.

Catamenial Tampon for digital insertion with a bulge in the middle area.

4 Claims, 9 Drawing Figures

CATAMENIAL TAMPON

BACKGROUND OF THE INVENTION

This tampon has no applicator and therefore the neighboring sections of the rounded bulge in the central portion are both hard compressed. The fibers in the bulge of the tampon had been loosened which makes the tampon softer in the bulge than the hard compressed neighboring sections on both sides of the bulge. The bulge being softer than the remaining parts of the tampon, said bulge does not irritate the walls of the vagina. But said bulge just the same soakes up any liquid immediately, and faster than a compressed bulge, until the hard cylindrical sections of the tampon have expanded.

SUMMARY OF THE INVENTION

When the tampon is enclosed in a protective wrapper, called an umbrella wrapper, the bulge in the middle section of the tampon serves as a stop and guide to hold the tampon at its middle section. That leaves sufficient length of the hard pressed section underneath the protective wrapper to be grasp with security by the fingers. This prevents that the tampon inadvertently slips from the users hand and is dropped, whereupon it must be discarded. To let the tampon slip out of the fingers is almost unavoidable, if the fingers grip the tampon underneath the protective umbrella only at its very end. It is obvious that it is very important to be able to grasp the tampon underneath the protective wrapper umbrella immediately and always even accurately through the aid of the bulge in said middle section of the tampon. With it the fingers get a very good grip on the hard compressed section of the tampon.

The middle section of the tampon with its central rounded bulge with loosened fibers serving as a stop and guide, and defining a soft porous absorbent section. With this stop and guide the tampon is always accurately held at its middle section, the fingers lightly touching the beginning of the bulge. This is very important, as the tampon is used in connection with a protective umbrella of a substantially fluid impervious sheet material and at the middle section bulge stop said umbrella material is draped over the hand, when the fingers are in contact with the bulge. Also at this middle section stop position one finger pushes the tampon further into the vagina which automatically places the tampon so deep into the vagina, that the closing muscle which is at the entrance of the vagina, cannot press on the tampon, which eliminates a painful sensation.

Furthermore the tampon has at least some circumferentially spaced longitudinally extending compressed strips, whose fibre portions in the bulge area are loosely compacted.

The packaging of the tampon may include a two section cover means contoured to receive said tampon and having a telescoping joint at the middle portion of said bulge.

The above and other advantages, objects, and features attendant the improved device of this invention will become apparent by reference to the specification and accompanying drawing.

DESCRIPTION OF THE PREFERRED EMBODIMENTS

Figure 1:
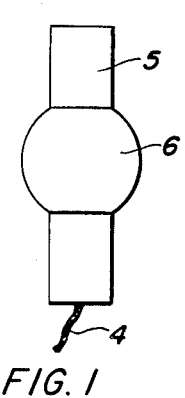
FIG. 1 illustrates the tampon with the central rounded bulge.

In FIG. 1 a compressed cylindrical tampon 5 having a central rounded bulge 6 and a withdrawal cord 4, the bulge consisting of loosened fibers.

Figure 2:
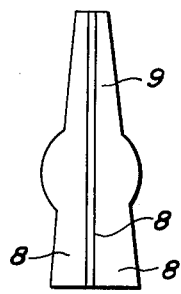
FIG. 2 shows the tampon having the shape of a cone.

FIG. 2 shows the tampon 9 in the shape of a cone. Here too the bulge can be seen in the middle area of the tampon. The tampon has longitudinally extending compressed strips 8 whose fibre portions in the bulge area are loosely compacted.

Figure 3:
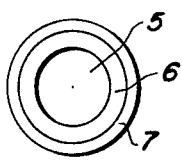
FIG. 3 is a cut through the bulge area of the tampon.

FIG. 3 illustrates a cut through FIG. 1. The cylindrical hard compressed body of the tampon is shown by 5 and the circumference of the bulge with loosened fibers is indicated by 6 and 7.

Figure 4:
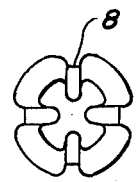
FIG. 4 is a cut through the bulge area of a differently shaped tampon.
Figure 7:
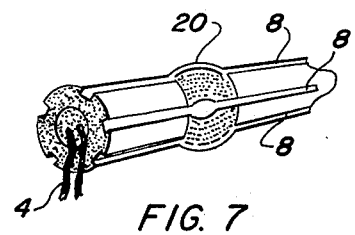
FIG. 7 shows circumferentially spaced longitudinally extending compressed strips on a tampon.

FIG. 4 illustrates a cut through the tampon seen in FIG. 7.

Figure 5:
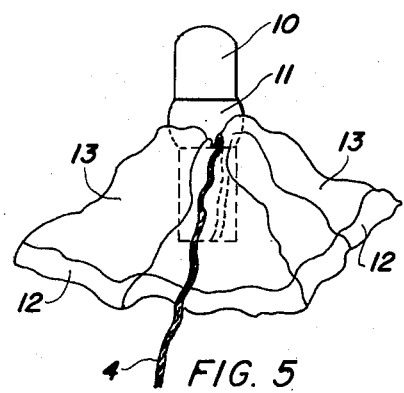
FIG. 5 is the tampon with a protective umbrella, the tampon showing the bulge.
Figure 6:
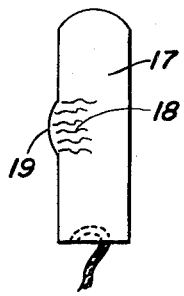
FIG. 6 shows the loosened fibres located at a central portion spaced from ends of the tampon.

This cut also shows the hard compressed strips 8. FIG. 5 shows tampon 10 with bulge 11 and protective umbrella 12 provided with an easy sliding material (Battist) 13, which alone comes in contact with the human skin. Tampon 10 is held below protective umbrella 12 with the hand that introduces the tampon into the human body without touching the skin. FIG. 6 shows tampon 17 with a bulge in the middle area of the tampon. This bulge is only on one side of the tampon. The lines 18 in this bulge 19 show how the cotton fibers in bulge 19 may be slightly loosened.

FIG. 7 shows a tampon with circumferentially spaced longitudinally extending compressed strips 8, with fibre portions in the bulge 20 loosely compacted. This is indicated by a small oval shape of said strip 8 in the middle section of bulge 20, with it creating a slightly softer surface of the bulge than the remaining part of the tampon. In the cylindrical tampon parts the highly compressed strips 8 remain intact and are not broken.

Figure 8:
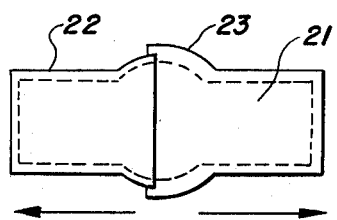
FIGS. 8 and 9 show a tampon including a two section cover tube with telescoping joint at the midportion of the bulge.

FIG. 8 shows with 22 the left side of a plastic tube and with 23 the right side of said tube. 21 is the tampon inside the tube.

Figure 9:
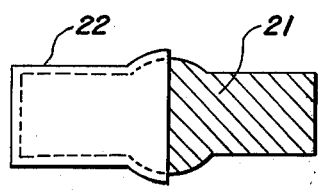

FIG. 9 shows the right side of the tampon with the right side of the plastic tube section taken off.

It is understood that the invention is not limited specifically to the preferred embodiments set forth above, and that suitable changes, modifications, and variations may be made without departing from the spirit and scope of the invention as defined in the appended claims.

What I claim is:

1. A catamenial tampon for digital insertion comprising a compressed cylindrical body of absorbent fibre material having an insertion end and a withdrawal end, a means for obstructing and absorbing body fluid flow comprising a central rounded bulge means of loosened fibres located at a central portion spaced from ends and defining a soft porous absorbent section for contacting the vaginal walls.

2. The tampon of claim 1 including a means for protecting and shielding the hand comprising a flexible substantially fluid impervious sheet material umbrella means attached around said cylindrical body adjacent the portion of said bulge means facing said withdrawal end and arranged to drape over the hand when the fingers are in contact with the bulge.

3. The tampon of claim 1 including at least four circumferentially spaced longitudinally extending compressed strips whose fibre portions in the bulge area are loosely compacted.

4. The tampon of claim 1 further including a two section cover means contoured to receive said tampon and having a telescoping joint at the midportion of said bulge means.

* * * * *